(12) United States Patent
Choi

(10) Patent No.: US 8,529,876 B2
(45) Date of Patent: Sep. 10, 2013

(54) PIGMENT MIXTURES FOR COSMETICS

(75) Inventor: Sung Yuen Choi, Tarrytown, NY (US)

(73) Assignee: BASF Corporation, Florham Park, NJ (US)

(*) Notice: Subject to any disclaimer, the term of this patent is extended or adjusted under 35 U.S.C. 154(b) by 0 days.

(21) Appl. No.: 13/396,580

(22) Filed: Feb. 14, 2012

(65) Prior Publication Data

US 2012/0207802 A1 Aug. 16, 2012

Related U.S. Application Data

(60) Provisional application No. 61/443,100, filed on Feb. 15, 2011.

(51) Int. Cl.
*A61K 8/00* (2006.01)
*A61K 8/18* (2006.01)

(52) U.S. Cl.
USPC .......................................................... 424/69

(58) Field of Classification Search
None
See application file for complete search history.

(56) References Cited

U.S. PATENT DOCUMENTS

| | | | |
|---|---|---|---|
| 3,087,829 A | 4/1963 | Linton | |
| 3,331,699 A | 7/1967 | Marshall et al. | |
| 4,753,829 A | 6/1988 | Panush | |
| 5,085,706 A * | 2/1992 | Kuske et al. | 106/456 |
| 5,273,576 A * | 12/1993 | Sullivan et al. | 106/418 |
| 5,441,564 A * | 8/1995 | Vogt | 106/417 |
| 5,958,125 A | 9/1999 | Schmid et al. | |
| 6,045,914 A | 4/2000 | Sullivan et al. | |
| 6,334,893 B1 * | 1/2002 | Pfaff et al. | 106/442 |
| 6,517,628 B1 * | 2/2003 | Pfaff et al. | 106/417 |
| 6,632,275 B1 * | 10/2003 | Schoen et al. | 106/404 |
| 6,875,264 B2 | 4/2005 | Zimmermann et al. | |
| 7,156,913 B2 * | 1/2007 | Pfaff et al. | 106/457 |
| 7,351,474 B2 | 4/2008 | Etzrodt et al. | |
| 7,507,285 B2 | 3/2009 | Venturini et al. | |
| 7,604,862 B2 * | 10/2009 | Ambrosius et al. | 428/404 |
| 7,887,849 B2 * | 2/2011 | Heinz et al. | 424/646 |
| 2004/0191198 A1 * | 9/2004 | Hochstein et al. | 424/63 |
| 2007/0048237 A1 | 3/2007 | Song et al. | |
| 2008/0305184 A1 * | 12/2008 | Heinz et al. | 424/646 |
| 2008/0318012 A1 * | 12/2008 | Domnick et al. | 428/216 |
| 2009/0220557 A1 * | 9/2009 | Pfaff et al. | 424/401 |
| 2009/0246294 A1 | 10/2009 | Hochstein et al. | |
| 2010/0011992 A1 * | 1/2010 | Bujard et al. | 106/439 |
| 2010/0196296 A1 * | 8/2010 | Geissler et al. | 424/61 |

FOREIGN PATENT DOCUMENTS

| | | |
|---|---|---|
| EP | 0803550 A2 * | 8/1999 |
| EP | 2075290 A2 * | 7/2009 |
| WO | WO 2004061012 A2 * | 7/2004 |
| WO | WO2008083894 | 7/2008 |
| WO | WO2009053391 | 4/2009 |

OTHER PUBLICATIONS

Duncan D.R. The Colour of Pigment Mixtures. Proc. Phys. Soc. 1940, 52(3):390-401.*
BASF News Release 'BASF Introduces Lumina® Royal Blue Effect Pigments' Nov. 19, 2009, [online], [retrieved on Feb. 8, 2011] Retrieved from the BASF website using Internet <URL:http://www2.basf.us/corporate/news_2009/news_release_2009_00249.htm>.
BASF News Release 'BASF Introduces high-chroma effect pigments—Lumina® Royal Blue' Jan. 27, 2010, [online], [retrieved on Feb. 8, 2011] Retrieved from the BASF website using Internet <URL:http://www.dispersions-pigments.basf.com/portal/basf/ien/dt.jsp?setCursor=1_422182_491010>.
'High chroma pigments for majestic effects—Lumina® Royal Blue' [online], [retrieved Feb. 3, 2012] Retrieved from the BASF website using Internet URL <http://www.dispersions-pigments.basf.com/portal/load/fid601672/LuminaRoyalBlueIndustrial.pdf>.
Lumina® Royal Blue EH 627 (9680H), Technical Data Sheet, BASF, Oct. 2009 Rev 2, 4 pages.
Lumina® Russet 9450D, Technical Data Sheet, BASF, Aug. 2009 Rev 1, 3 pages.

* cited by examiner

*Primary Examiner* — Robert A Wax
*Assistant Examiner* — Olga V Tcherkasskaya
(74) *Attorney, Agent, or Firm* — Anna-Lisa Gallo

(57) ABSTRACT

Provided is a pigment composition comprising a first and second effect pigments, wherein the composition has a hue comparable to carmine but does not comprise carmine.

10 Claims, 1 Drawing Sheet

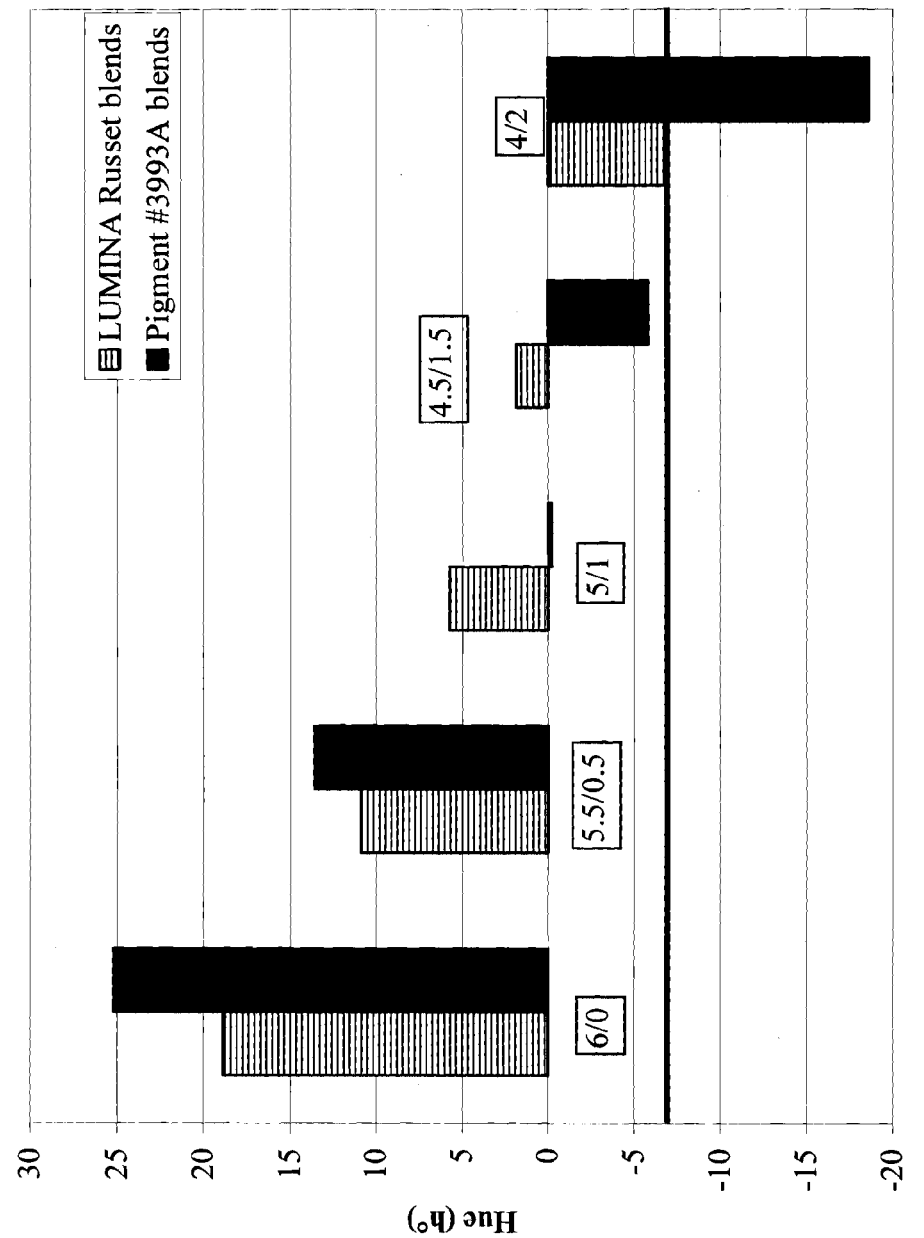

PIGMENT MIXTURES FOR COSMETICS

CROSS-REFERENCE TO RELATED APPLICATIONS

This application claims the benefit pursuant to 35 U.S.C. §119(e) of U.S. Provisional Application No. 61/443,100, filed Feb. 15, 2011.

BACKGROUND

Effect pigments, also known as pearlescent pigments or nacreous pigments, are used to impart a pearlescent luster, metallic luster, and/or multi-color effect approaching iridescence, to a material. For instance, red effect pigments based on flake-form substrates are important in cosmetics. Due to strict governmental regulation, the primary red effect pigments for cosmetic applications are carmine and $Fe_2O_3$-based pigments.

Carmine is a red organic pigment obtained from carminic acid produced by scale insects such as cochineals. Carmine can contribute to bluish-red shades. Effect pigments made with carmine often have a short shelf-life due to the degradation of carmine resulting from its uv-light susceptibility. In addition, there is concern that carmine might cause allergic reactions and therefore be hazardous when used as a dye in foodstuffs or cosmetics.

$Fe_2O_3$-based effect pigments tend to be very stable and not subject to decomposition the way carmine effect pigments are. The absorption component of hematite-$Fe_2O_3$ contributes red-orange hues. However, $Fe_2O_3$-based effect pigments do not provide the color intensity and brightness of carmine-based pigments.

There is an on-going need in the art for red pigment compositions with improved properties.

SUMMARY

The following composition meet and address these needs. The following summary is not an extensive overview. It is intended to neither identify key or critical elements of the various contemplated compositions, not delineate the scope of them.

Provided is a composition comprising a first effect pigment and a second effect pigment, wherein the composition has a color angle of about 310 to about 20 and does not comprise carmine. The first effect pigment comprises a substrate and at least one layer comprising $Fe_2O_3$. The second effect pigment consists of a substrate and one or more colorless metal oxide layers.

The composition can have a color angle of about 340 to about 360. The composition can have a chroma of at least about 50.

The first effect pigment and the second effect pigment can be present in the composition in a ratio of about 2:1 to about 5:1 by weight. Alternatively, the first effect pigment can be present in the composition at about 65% to about 85% by weight. Additionally, the second effect pigment can be present in the composition at about 15% to about 35% by weight.

The first effect pigment can have a color angle of about 10 to about 25. The substrate of the first effect pigment can be mica, and the substrate has a single layer of $Fe_2O_3$. Also contemplated, the substrate of the first effect pigment can be mica, and the substrate comprises at least one layer of $Fe_2O_3$, at least one layer of silicon dioxide and at least one layer of titanium dioxide. Contemplated first effect pigments include: substrate/$TiO_2$/$SiO_2$/$Fe_2O_3$/$SiO_2$/$TiO_2$; substrate/$Fe_2O_3$/$SiO_2$/$Fe_2O_3$/$SiO_2$/$TiO_2$; substrate/$SiO_2$/$Fe_2O_3$; substrate/$TiO_2$/$SiO_2$/$Fe_2O_3$; substrate/$Fe_2O_3$/$SiO_2$; substrate/$Fe_2O_3$/$SiO_2$/$Fe_2O_3$; substrate/$Fe_2O_3$/$SiO_2$/$TiO_2$; substrate/$Fe_2O_3$/$SiO_2$/$TiO_2$/$SiO_2$/$TiO_2$; and substrate/$TiO_2$/$SiO_2$/$TiO_2$/$SiO_2$/$Fe_2O_3$.

The second effect pigment has a color angle of about 260 to about 310. The substrate of the second effect pigment can be mica, and the second effect pigment can comprise a layer of rutile titanium dioxide.

Also provided is a cosmetic composition comprising a first effect pigment and a second effect pigment, wherein the composition has a color angle of about 310 to about 20 and does not comprise carmine. A cosmetic composition optionally comprises at least one cosmetically-acceptable auxiliary agent.

BRIEF DESCRIPTION OF THE DRAWINGS

For the purpose of illustrating the various compositions and methods, there are depicted in the drawings certain compositions. However, the compositions and their methods of use are not limited to the precise arrangements and instrumentalities of the compositions depicted in the drawings.

The FIGURE depicts a bar graph depicting color angle data for various exemplary pigments compositions. The X-axis is the ratio of component A (either LUMINA Russet 9450D or Pigment #3993A) to component B (LUMINA Royal Blue). The thick horizontal line at −10 color angle indicates the hue of CLOISONNE Super Red, a carmine-based effect pigment.

DETAILED DESCRIPTION

There is a need in the art to provide red effect pigments for cosmetics that cover the same hue range as carmine-based effect pigments but possess longer shelf life compared to carmine-based pigments. Provided herein is a pigment composition comprising a mixture of effect pigments that meets these needs.

Effect pigments are composed of a plurality of laminar platelets, each of which is coated with one or more reflecting/transmitting layers. Typically, effect pigments are a laminar platy substrate such as mica or glass flake that has been coated with a metal oxide layer. A description of effect pigments' properties can be found in the PIGMENT HANDBOOK, Volume I, Second Edition, pp. 829-858, John Wiley & Sons, NY 1988, which is incorporated herein by reference. If colorless metal oxides are used, effect pigments exhibit pearl-like luster as a result of reflection and refraction of light, and depending on the thickness of the metal oxide layer, they can also exhibit interference color effects. If colored metal oxides are used, the observed effects depend on reflection, refraction and absorption.

The pigment composition can comprise a first effect pigment and a second effect pigment, wherein the first effect pigment comprises at least one layer comprising $Fe_2O_3$ and wherein the second effect pigment consists of one or more colorless metal oxide layers. The first effect pigment has a red hue, and the second effect pigment has a blue hue. The compositions can comprise the first and second effect pigments, which can have a hue similar to carmine-based pigments but do not contain carmine. Accordingly, the pigment compositions are not subject to the uv-light and storage instability of carmine-based pigments and are expected to have increased stability as a result. In addition, the claimed pigment compositions can have greater chroma than carmine-based pigments. Greater chroma provides improved color intensity and brightness relative to carmine-based pigments.

Color can be described in different color space systems, such as CIELAB. As discussed herein, color of the pigment composition is described in terms of hue and chroma. Hue is the attribute that permits colors to be classed as red, yellow, blue, and so on. As used herein, color angle h° is a measure of hue, scaled from 0 to 360 degrees. Chroma ("C*") indicates the saturation, intensity or purity of a color. Colors with strong chroma are the most brilliant. As used herein, the color data is obtained from drawdowns formulated with pigments at 6% by weight dispersed in a nitrocellulose lacquer system, dried, and measured by X-Rite MA 68 at 45 degree incident angle and measured at +15 degrees. Conversion to other color space systems can be done using calculations known in the art.

The hue of the claimed composition can be about 310 to about 20, about 340 to about 20, about 340 to about 360, or about 345 to about 355, or about 350. The chroma of the claimed composition can be at least about 50, at least about 55, or at least about 57. The composition can have a hue of about 354 and a chroma of at least about 50. The composition can have a hue of about 354 and a chroma of at least about 57. Alternatively, the composition has a hue of about 341 and a chroma of at least about 50. The composition can have a hue of about 341 and a chroma of at least about 58. Alternatively, the composition can have a hue of about 353 and a chroma of at least about 50. The composition can have a hue of about 353 and a chroma of at least about 56.

The claimed composition comprises from about 5% to about 95%, about 65% to about 85% or about 66% to about 75% by weight of a first effect pigment and from about 5% to about 95%, about 15% to about 35% or about 25% to about 34% by weight of a second effect pigment, with respect to the total composition weight. The composition can comprise about 92% by weight of the first effect pigment and about 8% by weight of the second effect pigment. Additionally, the composition can comprise about 83% by weight of the first effect pigment and about 17% by weight of the second effect pigment. Another composition can comprise about 75% by weight of the first effect pigment and about 25% by weight of the second effect pigment. Yet another composition can comprise about 66% by weight of the first effect pigment and about 34% by weight of the second effect pigment.

The composition can further at least one additional component, in which the ratio of the first pigment to the second pigment can range from about 2:1 to about 5:1. The at least one additional component is an effect pigment. Alternatively, the at least one additional component excludes an effect pigment.

The pigments can be mixed in any convenient fashion to prepare the claimed compositions. No special procedures are required.

The first pigment in the claimed composition comprises at least one layer comprising $Fe_2O_3$ on a platy substrate. The first pigment can consist of a single layer of $Fe_2O_3$ on a platy substrate. The first pigment can consist of substrate/$Fe_2O_3$ and has a particle size distribution (D20) of about 20 micrometers. The first pigment can comprise substrate/$Fe_2O_3$ and can have a particle size distribution (D20) of about 20 micrometers. The first pigment can comprise or consist of a layer that is a mixture of $Fe_2O_3$ and one or more other oxides. Effect pigments suitable as the first pigment in the claimed composition are disclosed, for instance, in U.S. Pat. Nos. 3,087,829; 3,331,699; 5,958,125; 6,045,914; and 6,875,264.

The first pigment can be iron oxide-coated mica. An exemplary iron oxide-coated mica is LUMINA Russet 9540D (BASF, Florham Park, NJ). This pigment has a particle size distribution (D50) of about 21 micrometers; about 95% of the platelets are between about 8 to 48 micrometer in major dimension by light scattering measurement.

Alternatively, the first pigment can comprise multiple layers in which at least one layer comprises or consists of iron oxide. The multiple layers can alternate high refractive index oxide and low refractive index materials, wherein at least one high refractive index layer is $Fe_2O_3$ (iron oxide; refractive index 3.02). The high refractive index materials can also include, but are not limited to, anatase titanium dioxide (2.55), rutile titanium dioxide (2.90), zirconium dioxide (2.20), zinc oxide (2.03), zinc sulfide (2.38), bismuth oxychloride (2.15) or the like. The low refractive index material can include, but is not limited to, silicon dioxide (refractive index 1.46), magnesium fluoride (1.39), aluminum oxide (1.76), a polymer such as polymethyl methacrylate, polystyrene, ethylene vinyl acetate, polyurea, polyurethane, polydivinyl benzene (1.4-1.6 typical refractive index for polymers) and the like. Refractive indices are available in the CRC HANDBOOK OF CHEMISTRY AND PHYSICS, Haynes editor, 91$^{st}$ edition, 2011. Exemplary combinations of metal oxides for the first pigment include: substrate/$TiO_2$/$SiO_2$/$Fe_2O_3$/$SiO_2$/$TiO_2$; substrate/$Fe_2O_3$/$SiO_2$/$Fe_2O_3$/$SiO_2$/$TiO_2$; substrate/$SiO_2$/$Fe_2O_3$; substrate/$TiO_2$/$SiO_2$/$Fe_2O_3$; substrate/$Fe_2O_3$/$SiO_2$; substrate/$Fe_2O_3$/$SiO_2$/$Fe_2O_3$; substrate/$Fe_2O_3$/$SiO_2$/$TiO_2$; substrate/$Fe_2O_3$/$SiO_2$/$TiO_2$/$SiO_2$/$TiO_2$; and substrate/$TiO_2$/$SiO_2$/$TiO_2$/$SiO_2$/$Fe_2O_3$. Alternatively, the first pigment comprises substrate/$TiO_2$/$SiO_2$/$TiO_2$/$SiO_2$/$Fe_2O_3$ and has a particle size distribution (D50) of about 17 micrometers.

With any of the described first pigments, hue of the first pigment can be about 10 to about 25, about 15 to about 25, or about 19 to about 25. The first pigment can have a hue of about 19. Alternatively, the first pigment can have a hue of about 19 and a chroma of at least 50. The first pigment can also have a hue of about 19 and a chroma of about 66. Additionally, the first pigment can have a hue of about 25. Also, the first pigment can have a hue of about 25 and a chroma of at least 50. The first pigment can have a hue of about 25 and a chroma of about 65.

The second pigment of the claimed composition is an effect pigment consisting of one or more layers of colorless and transparent metal oxide layers on a platy substrate. Exemplary metal oxides for the second pigment include titanium dioxide, silicon dioxide, zirconium dioxide, zinc oxide, and aluminum oxide. The second pigment can comprise at least one layer of rutile titanium dioxide on a mica substrate. The second pigment can comprise alternating layers of titanium dioxide and silicon dioxide on a substrate, such as substrate/$TiO_2$/$SiO_2$/$TiO_2$. In some aspects, as least one $TiO_2$ layer of the substrate/$TiO_2$/$SiO_2$/$TiO_2$ second pigment can comprise or consist of rutile $TiO_2$.

The hue of the second pigment can be about 260 to about 310, about 270 to about 285 or about 275 to about 280. The second pigment can have a hue of about 277. The second pigment can have a hue of about 277 and a chroma of at least 60. The second pigment can have a hue of about 277 and a chroma of about 60. Alternatively, the second pigment can have a hue of about 304 and a chroma of at least 70. Or, the second pigment can have a hue of about 275 to 277 and a chroma of about 73 to 77.

The composition can comprise a first pigment having a hue of about 18-19 and a second pigment having a hue about 277, and the composition can have a hue of 350 to 20. The chroma of this composition can be at least about 55, or the chroma can be at least about 55 to about 62. The composition can comprise a first pigment having a hue of about 25 and a second pigment having a hue about 277, and the composition can have a hue of 340 to 25. The chroma of this composition can be at least about 57, or the chroma can be at least about 57 to about 62. Additionally, the composition can comprise a first pigment having a hue of about 18-19 and a second pigment having a hue about 275 to 278, and the composition has a hue of 345 to 355. The chroma of this composition can be at least about 52, or the chroma can be at least about 52 to about 57.

Particle size distribution of effect pigments is not critical. Effect pigments having a narrow particle size distribution can be used. The first and/or second pigments can have a particle size distribution (D50) of about 4 to about 75, or about 15 to about 25.

The composition can comprise the first effect pigment and the second effect pigment in a ratio of about 5:1 to about 2:1, wherein the first effect pigment is a mica-based pigment having a hue of about 19 to about 25 and wherein the second effect pigment is a mica-based pigment having a hue of about 270 to about 285, of about 275 to about 280 or about 277, and does not comprise carmine. The second effect pigment can comprise at least one layer of rutile titanium dioxide and optionally at least one layer of silicon dioxide. The composition can have a hue of about 340 to about 20, about 340 to about 360, about 345 to about 355, or about 350. The composition can have a chroma of at least about 56, at least about 57 or at least about 58. The composition can possess improved uv-stability compared to carmine, and can have improved storage stability.

An effect pigment useful in the claimed pigment composition can be formed by any process known in the art. It can be accomplished, as one example, by precipitating a metal ion with hydroxide onto laminar platy substrate particulate, and thereafter, calcining the coated particulates to provide metal oxide-coated flake-form pigment. Metal oxides useful for preparing effect pigments include titanium oxide, iron oxide, and silicon oxide.

In general, the procedure for preparing effect pigments involves dispersing the platy material particulates and combining that dispersion with a precursor, which results in the formation of a precursor coating on the particulates. For instance, in the case of titanium, titanyl chloride or titanium tetrachloride can be used and in the case of iron, the source material can be ferric chloride. The pH of the resulting slurry is maintained at an appropriate level during the addition of the titanium or iron salt by the use of a suitable base such as sodium hydroxide in order to cause precipitation of a titanium dioxide or iron oxide precursor on the particulate. If desired, layers of titanium and iron hydroxide and/or oxide (or other metals) can be deposited sequentially.

The average particle size of the particulates can vary from an average of about 3 microns to an average of about 100 microns, although smaller flakes of down to about 1 micron and less or larger flakes of up to 150 microns or more can also be used if desired. The platy particulate can have a thickness of about 0.1 to 10 micrometer and an aspect ratio (average particle size/thickness) of at least about 10. The concentration of the particulate in the water can vary from about 5 to 60%, or from about 10 and 20%. Narrow particle size distributions can be advantageous.

Other coating procedures, such as for example, chemical vapor deposition processes, can also be used to prepare effect pigments useful in the claimed composition.

Examples of useful platy materials include platy aluminum oxide, platy glass, aluminum, natural mica, synthetic mica, bismuth oxychloride, platy iron oxide, platy graphite, platy silica, bronze, stainless steel, natural pearl, boron nitride, silicon dioxide, copper flake, copper alloy flake, zinc flake, zinc alloy flake, zinc oxide, enamel, china clay, porcelain, and combinations thereof. The first effect pigment and/or the second effect pigment comprise mica as the platy substrate.

Effect pigments suitable for creating the pigment composition claimed are commercially available. The effect pigments include those available from BASF Corporation under the tradenames LUMINA, LUMINA ROYAL, BIJU, CLOISSONE, DUOCROME, FLAMENCO, TIMICA, and REFLECKS. It is understood that the claimed composition can comprise pigment that are not commercially available.

The pigment compositions disclosed can be used in any application benefiting from a red color. Such applications include, but are not limited to, cosmetics, paints, ink jet printing, for dyeing textiles, for pigmenting coatings (paints), printing inks, plastics, glazes for ceramics and glass, and the like.

The composition can be part of a cosmetic composition. The form of the cosmetic composition can be any form normally used for cosmetics such as cream, emulsion, foam, gel, lotion, milk, mousse, ointment, paste, powder, spray, or suspension. The cosmetic composition can be any colored cosmetic used on the skin, hair, eyes, or lips, such as concealing sticks, foundation, stage make-up, mascara (cake or cream), eye shadow (liquid, pomade, powder, stick, pressed or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, perfume lotion, and shampoos of all types (gel or liquid). In addition, the claimed compositions can be used in shaving cream (concentrate for aerosol, brushless, lathering), hair groom, cologne stick, cologne, cologne emollient, bubble bath, body lotion (moisturizing, cleansing, analgesic, astringent), after shave lotion, after bath milk and sunscreen lotion. For a review of cosmetic applications, see Cosmetics: Science and Technology, 2nd Ed., Eds: M. S. Balsam and Edward Sagarin, Wiley-Interscience (1972), and deNavarre, The Chemistry and Science of Cosmetics, 2nd Ed., Vols 1 and 2 (1962), Van Nostrand Co. Inc., Vols 3 and 4 (1975), Continental Press, both of which are hereby incorporated by reference.

The amount of the claimed pigment composition present in a cosmetic composition is dependent on the color cosmetic being created and the final form of the cosmetic. More pigment can be used to create higher intensity, or provide higher coverage or correction. One skilled in the art will be able to determine the appropriate amount of pigment to use based upon the desired properties of the colored cosmetic formulation; however, a colored cosmetic composition can comprise from about 0.005 to 99.9%, about 0.05 to about 50%, or about 0.1 to about 10% by weight of the claimed pigment composition, based on the total weight of the cosmetic composition.

The cosmetic composition optionally comprises at least one cosmetically acceptable auxiliary agent. Cosmetically acceptable auxiliary agents include, but are not limited to, carriers, excipients, emulsifiers, surfactants, preservatives, fragrances, perfume oils, thickeners, polymers, gel formers, dyes, absorption pigments, photoprotective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous or antiallergic active ingredients and mixtures thereof. Cosmetic formulations are known in the art. See, for instance, US Publication Nos. 20080196847 and 20100322981.

EXAMPLES

The compositions and methods of use are further described in detail by reference to the following experimental examples. These examples are provided for purposes of illustration only, and are not intended to be limiting unless otherwise specified. Thus, the compositions and methods of use should in no way be construed as being limited to the following examples, but rather, should be construed to encompass any and all variations which become evident as a result of the teaching provided herein.

Compositions were prepared comprising two effect pigments, designated components A and B.

Example 1

In the first series, the compositions were mixtures of LUMINA Russet 9450D (component A; BASF, Florham Park, N.J.) and LUMINA Royal Blue EH627 (component B; BASF, Florham Park, N.J.). LUMINA Russet 9450D is a $Fe_2O_3$-coated mica pigment having a particle size distribution (D50) of about 21 micrometers and exhibiting a hue of 19 and chroma of 66. LUMINA Royal Blue EH627 is a titanium dioxide/silicon dioxide/titanium dioxide coated mica pigment having a particle size distribution (D50) of about 17 micrometers and exhibiting a color angle of 277 and a chroma of 77.

Hue angle h° and chroma C* were assessed for the mixtures using drawdowns formulated with the pigment mixture at 6% by weight dispersed in a nitrocellulose lacquer system, dried, and measured by X-Rite Multi-Angle Spectrophotometer MA 68 (X-Rite, Grand Rapids, MI) at 45 degree incident angle and measured at +15 degree. Chroma values (C*) are scaled between 0 and 100, wherein an increase in chroma corresponds to an increase in saturation or brilliance. The color angle is scaled between 0 and 360 degrees, wherein 0 and 360 are the same color (red). Thus, a h° of −20 is the same as a h° of 340 (i.e., 360-20). In the tables below, the corresponding positive) (h° is provided in parentheses for negative h°.

The data are summarized in Table 1. The h° and C* of CLOISONNE Super Red ("carmine"; BASF, Florham Park, N.J.), a carmine/titanium dioxide coated mica, are also listed.

TABLE 1

| Sample # | Ratio of A:B | h° | C* |
|---|---|---|---|
| Control 1 | 6:0 | 18.88 | 66 |
| 1 | 5.5:0.5 | 10.9 | 61.48 |
| 2 | 5:1 | 5.73 | 59.66 |
| 3 | 4.5:1.5 | 1.86 | 59.54 |
| 4 | 4:2 | −7 (353) | 56.84 |
| Carmine | n/a | 353 | 48 |

As the amount of LUMINA Royal Blue EH627 increased in the mixtures, h° varied from 19 to 353 and C* varied from 66 to 57. For instance, Sample 4 having about 66% component A and about 34% component B, exhibited the same hue as carmine and advantageously exhibited greater chroma.

Example 2

In the second series, the compositions were mixtures of pigment #3993 (component A) and LUMINA Royal Blue EH627 (component B). Pigment #3993 is a multi-layered red pigment wherein the first layer is $Fe_2O_3$, having a particle size distribution (D50) of about 17 micrometers, and which exhibits a color angle of 25 and a chroma of 65. The h° and C* was assessed for the mixtures as described in Example 1. The data are summarized in Table 2, which also includes the data for CLOISONNE Super Red.

TABLE 2

| Ex. # | Ratio of A:B | h° | C* |
|---|---|---|---|
| Control 2 | 6:0 | 25.19 | 65 |
| 5 | 5.5:0.5 | 13.6 | 61.95 |
| 6 | 5:1 | −0.18 (360) | 59.29 |
| 7 | 4.5:1.5 | −5.82 (354) | 57.46 |
| 8 | 4:2 | −18.6 (341) | 58.19 |
| Carmine | n/a | 353 | 48 |

As the amount of LUMINA Royal Blue EH627 increased in the mixtures, h° varied from 25 to 341 and C* varied from 65 to 58. Sample 7, having about 75% component A and about 25% component B, exhibited a hue comparable to carmine and also exhibited greater chroma relative to carmine.

The hue data for the compositions in Tables 1 and 2 are also depicted as a bar graph in the FIGURE. The solid horizontal line at −7 (353) indicates the hue of carmine.

Example 3

In the third series, the compositions were 2:1 mixtures of LUMINA Russet 9450D (component A; BASF, Florham Park, N.J.) and LUMINA Royal Blue 9680H (component B; BASF, Florham Park, N.J.). Four different lots of LUMINA Russet 9450D and two different lots of LUMINA Royal Blue 9680H were used. As discussed above, LUMINA Russet 9450D is a $Fe_2O_3$-coated mica pigment having a particle size distribution (D50) of about 21 micrometers. The hue and chroma for the four lots of LUMINA Russet 9450D are shown in Table 3.

TABLE 3

| Lot | h° | C* |
|---|---|---|
| 1R | 18.88 | 66.45 |
| 2R | 18.15 | 62.08 |
| 3R | 18.13 | 61.38 |
| 4R | 18.28 | 61.45 |

LUMINA Royal Blue 9680H is a titanium dioxide/silicon dioxide/titanium dioxide coated mica pigment having a particle size distribution (D50) of about 17 micrometers. Table 4 comprises the hue and chroma of the two lots of LUMINA Royal Blue 9680H.

TABLE 4

| Lot | h° | C* |
|---|---|---|
| 1B | 277.53 | 77.79 |
| 2B | 275.19 | 73.24 |

Hue angle h° and chroma C* were assessed for the 2:1 (component A: component B) mixtures using drawdowns formulated with the pigment mixture at 6% by weight dispersed in a nitrocellulose lacquer system, dried, and measured by X-rite Multi-Angle Spectrophotometer MA 68. As in EXAMPLES 1 and 2, chroma values (C*) are scaled between 0 and 100, wherein an increase in chroma corresponds to an increase in saturation or brilliance. The color angle is scaled between 0 and 360 degrees, wherein 0 and 360 are the same color (red). Thus, a h° of −20 is the same as a h° of 340 (360-20).

The data for the various compositions are summarized in Table 5. The h° and C* of CLOISONNE Super Red ("carmine"; BASF, Florham Park, N.J.), a carmine/titanium dioxide coated mica, are also listed.

TABLE 5

| Sample# | Lot# of 9450D | Lot# of 9680H | h° | C* |
|---|---|---|---|---|
| 8 | 1R | 1B | 349.52 | 56.96 |
| 9 | 1R | 2B | 349.37 | 55.85 |
| 10 | 3R | 1B | 346.71 | 53.38 |
| 11 | 3R | 2B | 347.88 | 52.83 |
| 12 | 4R | 1B | 350.22 | 54.13 |
| 13 | 4R | 2B | 348.55 | 53.78 |
| 14 | 2R | 1B | 348.67 | 54.05 |
| 15 | 2R | 2B | 347.15 | 53.50 |
| Carmine | n/a | n/a | 353 | 48 |

The h° of the 2:1 mixtures of various pigment lots varied from 347 to 350, while C* varied from 53 to 57. Sample 12 exhibited a hue close to that of carmine and exhibited a greater chroma relative to carmine.

The disclosures of each and every patent, patent application, and publication cited herein are hereby incorporated herein by reference in their entirety.

While the compositions and their methods of use have been disclosed with reference to specific embodiments, it is apparent that other embodiments and variations may be devised by others skilled in the art without departing from the true spirit and scope of the described compositions, kits and methods of use. The appended claims are intended to be construed to include all such embodiments and equivalent variations.

What is claimed is:

1. A UV-stable pigment composition comprising:
   a first effect pigment and a second effect pigment,
   wherein the first effect pigment comprises a substrate and at least one layer comprising $Fe_2O_3$, and said first effect pigment has a color angle of about 10 to about 25;
   wherein the second effect pigment consists of a substrate and one or more colorless metal oxide layers, and said second effect pigment has a color angle of about 260 to about 310; and
   wherein said UV-stable composition has a color angle of about 340 to about 360, a color chroma of at least about 50, is not subject to UV-light instability, and does not comprise carmine.

2. The composition of claim 1, wherein the first effect pigment and the second effect pigment are present in the composition in a ratio of about 2:1 to about 5:1 by weight.

3. The composition of claim 1, wherein the first effect pigment is present in the composition at about 65% to about 85% by weight.

4. The composition of claim 1, wherein the second effect pigment is present in the composition at about 15% to about 35% by weight.

5. The composition of claim 1, wherein said substrate of said first effect pigment is mica and said substrate has a single layer of $Fe_2O_3$.

6. The composition of claim 1, wherein said substrate of said first effect pigment is mica and said substrate comprises at least one layer of $Fe_2O_3$, at least one layer of silicon dioxide ($SiO_2$) and at least one layer of titanium dioxide ($TiO_2$).

7. The composition of claim 1, wherein said substrate of said second effect pigment is mica and said second effect pigment comprises a layer of rutile titanium. dioxide.

8. The composition of claim 1, wherein said first effect pigment is selected from the group consisting of: substrate/$TiO_2$/$SiO_2$/$Fe_2O_3$/$SiO_2$/$TiO_2$; substrate/$Fe_2O_3$/$SiO_2$/$Fe_2O_3$/$SiO_2$/$TiO_2$; substrate/$SiO_2$/$Fe_2O_3$; substrate/$TiO_2$/$SiO_2$/$Fe_2O_3$; substrate/$Fe_2O_3$/$SiO_2$; substrate/$Fe_2O_3$/$SiO_2$/$Fe_2O_3$; substrate/$Fe_2O_3$/$SiO_2$/$TiO_2$; substrate/$Fe_2O_3$/$SiO_2$/$TiO_2$/$SiO_2$/$TiO_2$; and substrate/$TiO_2$/$SiO_2$/$TiO_2$/$SiO_2$/$Fe_2O_3$.

9. A cosmetic composition comprising the composition of claim 1 and optionally at least one cosmetically-acceptable auxiliary agent.

10. A UV-stable composition comprising: a first effect pigment and a second effect pigment,
   wherein the first effect pigment comprises a substrate and at least one layer comprising $Fe_2O_3$, and said first effect pigment has a color angle of about 10 to about 25;
   wherein the second effect pigment consists of a substrate and one or more colorless metal oxide layers, and said second effect pigment has a color angle of about 260 to about 310; and
   wherein said UV-stable composition has a color of an angle of about 340 to about 360, a color chroma of at least 50, and does not comprise carmine, and
   wherein the color angle and chroma of the UV-stable composition are not changed by UV irradiation.

* * * * *